US012678416B2

(12) United States Patent
Pantos et al.

(10) Patent No.: US 12,678,416 B2
(45) Date of Patent: Jul. 14, 2026

(54) L-TRIIODOTHYRONINE (T3) FOR USE IN LIMITING MICROVASCULAR OBSTRUCTION

(71) Applicants:UNI-PHARMA KLEON TSETIS PHARMACEUTICAL LABORATORIES S.A., Attica (GR); Ioulia Tseti, Attica (GR)

(72) Inventors: Constantinos Pantos, Kantza (GR); Iordanis Mourouzis, Korydallos (GR)

(73) Assignees: Ioulia TSETI, Attica (GR); Uni-Pharma Kleon Tsetis Pharmaceuticals Laboratories S.A., Attica (GR)

( * ) Notice: Subject to any disclaimer, the term of this patent is extended or adjusted under 35 U.S.C. 154(b) by 1160 days.

(21) Appl. No.: 17/414,278

(22) PCT Filed: Dec. 27, 2019

(86) PCT No.: PCT/EP2019/087056
§ 371 (c)(1),
(2) Date: Jun. 15, 2021

(87) PCT Pub. No.: WO2020/144073
PCT Pub. Date: Jul. 16, 2020

(65) Prior Publication Data
US 2022/0062214 A1 Mar. 3, 2022

(30) Foreign Application Priority Data

Jan. 9, 2019 (EP) ..................................... 19151064
Dec. 16, 2019 (EP) ..................................... 19386057

(51) Int. Cl.
*A61K 31/198* (2006.01)
*A61K 9/00* (2006.01)
*A61P 9/10* (2006.01)

(52) U.S. Cl.
CPC .............. *A61K 31/198* (2013.01); *A61P 9/10* (2018.01); *A61K 9/0019* (2013.01)

(58) Field of Classification Search
CPC ........ A61K 31/198; A61K 9/0019; A61P 9/10
(Continued)

(56) References Cited

U.S. PATENT DOCUMENTS

2005/0059574 A1 3/2005 Klein et al.
2011/0142947 A1 6/2011 Rubin et al.

FOREIGN PATENT DOCUMENTS

CN 103705497 A 4/2014
GR 1010068 B 9/2021
(Continued)

OTHER PUBLICATIONS

Khalife WI, et al. Treatment of subclinical hypothyroidism reverses ischemia and prevents myocyte loss and progressive LV dysfunction in hamsters with dilated cardiomyopathy. American Journal of Physiology-Heart and Circulatory Physiology. Dec. 2005; 289(6):H2409-15. (Year: 2005).*
(Continued)

*Primary Examiner* — Jeffrey S Lundgren
*Assistant Examiner* — Heather Dahlin
(74) *Attorney, Agent, or Firm* — DILWORTH IP, LLC

(57) ABSTRACT

The present invention concerns the use of L-triiodothyronine (T3) in a novel treatment to limit or prevent the occurrence of Microvascular Obstruction (MVO), after a successful Primary Percutaneous Coronary Intervention (PPCI), in the course of an acute ST-segment-elevation myocardial infarction (STEMI).

6 Claims, 8 Drawing Sheets

(58) Field of Classification Search

USPC ......................................................... 514/567

See application file for complete search history.

(56) References Cited

FOREIGN PATENT DOCUMENTS

| GR | 1010182 | B | | 3/2022 | | |
|----|---------|---|---|--------|---|---|
| GR | 1010261 | B | | 6/2022 | | |
| WO | 1995/00135 | A1 | | 1/1995 | | |
| WO | WO 95/00135 | A1 | * | 1/1995 | .......... | A61K 31/195 |
| WO | 95/24919 | A1 | | 9/1995 | | |
| WO | 2002/051403 | A1 | | 7/2002 | | |
| WO | 2017/075607 | A1 | | 5/2017 | | |
| WO | 2020/144073 | A1 | | 7/2020 | | |
| WO | 2021/127499 | A1 | | 6/2021 | | |

OTHER PUBLICATIONS

De Waha S et al. Relationship between microvascular obstruction and adverse events following primary percutaneous coronary intervention for ST-segment elevation myocardial infarction: an individual patient data pooled analysis from seven randomized trials. European heart journal. Dec. 14, 2017;38(47):35 (Year: 2017).*

Nicolini G, Forini F, Kusmic C, Pitto L, Mariani L, Iervasi G. Early and short-term triiodothyronine supplementation prevents adverse postischemic cardiac remodeling: role of transforming growth factor-β1 and antifibrotic miRNA signaling. Molecular Medicine. Jan. 2015;21:900-11. (Year: 2015).*

Pingitore A,et al. Usefulness of triiodothyronine replacement therapy in patients with ST elevation myocardial infarction and borderline/reduced triiodothyronine levels (from the THIRST study). The American journal of cardiology. Mar. 15, 2019;123(6):905-12. (Year: 2018).*

Hamilton MA, Stevenson LW, Fonarow GC, Steimle A, Goldhaber JI, Child JS, Chopra IJ, Moriguchi JD, Hage A. Safety and hemodynamic effects of intravenous triiodothyronine in advanced congestive heart failure. The American journal of cardiology. Feb. 15, 1998;81(4):443-7. (Year: 1998).*

Triiodothyronine for repair of left ventricular dysfunction and Remodeling in STEMI Patients, Thy-REPAIR clinical trial, EudraCT, URL:<https:/Avww.clinicaltrialsregister.eu/ctr-search/trial/20 16-000631-40/GR, Apr. 18, 2016 (Year: 2016).*

Occhipinti G, Strosio M, Rinaldi R, Ruberti A, Brugaletta S. Pharmacological and Interventional Prevention and Treatment of Microvascular Obstruction Following Primary PCI in STEMI. Journal of Cardiovascular Development and Disease. Nov. 2025;12(11):440. (Year: 2025).*

Rajagopalan V, Zhang Y, Pol C, Costello C, Seitter S, Lehto A, Savinova OV, Chen YF, Gerdes AM. Modified low-dose triiodo-L-thyronine therapy safely improves function following myocardial ischemia-reperfusion injury. Frontiers in Physiology. Apr. 12, 2017;8:225. (Year: 2017).*

Sabatino L, Kusmic C, Nicolini G, Amato R, Casini G, Iervasi G, Balzan S. T3 enhances Ang2 in rat aorta in myocardial I/R: comparison with left ventricle. Journal of Molecular Endocrinology. Jul. 21, 2016;57(3):139-49. (Year: 2016).*

Fracassi F, Niccoli G. Angiogenesis and microvascular obstruction: still a research topic or a new therapeutic target ?. Revista Espanola de Cardiologia (English ed.). Nov. 10, 2017;71(6):420-2. (Year: 2017).*

Makino A, Suarez J, Wang H, Belke DD, Scott BT, Dillmann WH. Thyroid hormone receptor-B is associated with coronary angiogenesis during pathological cardiac hypertrophy. Endocrinology. Apr. 1, 2009;150(4):2008-15. (Year: 2009).*

Triiodothyronine for repair of left ventricular dysfunction and Remodeling in STEMI Patients, Ty-REPAIR clinical trial, EudraCT, URL:<https://www.clinicaltrialsregister.eu/ctr-search/trial/2016-000631-40/GR, Apr. 18, 2016.

Elgendy, Islam Y., et al., "Microvascular obstruction in ST elevation myocardial infarction patients undergoing primary percutaneous coronary intervention: another frontier to conquer?", Journal of Thoracic Disease, vol. 10, No. 3, Mar. 2018, pp. 1343-1346.

De Waha, Suzzanne, et al., "Relationship between microvascular obstruction and adverse events following primary percutaneous coronary intervention for ST-segment elevation myocardial infarction: an individual patient data pooled analysis from seven randomized trials", European Heart Journal (2017) 38, pp. 3502-3510.

Nazir, Sheraz A., "Strategies to attenuate micro-vascular obstruction during P-PCI: the randomized reperfusion facilitated by local adjunctive therapy in ST-elevation myocardial infarction trial", European Heart Journal (2016) 37, pp. 1910-1919.

Pantos, Constantinos, et al., "Thyroid hormone receptor a1 as a novel therapeutic target for tissue repair:", Annals of Translational Medicine, atm.amegroups.com, 2018;6(12):254, 11 pages.

Mdzinarishvili, Alexander, et al., "Engineering triiodothyronine (T3) nanoparticle for use in ischemic brain stroke", Drug Deliv. and Transl. Res. (2013) 3: pp. 309-317.

Pantos, Constantinos, et al., "Translating thyroid hormone effects into clinical practice: the relevance of thyroid hormone receptor al in cardiac repair", Springer Science+Business Media New York, Dec. 11, 2014, 10 pages.

International Preliminary Report on Patentability in PCT/EP2019/087056; dated Aug. 19, 2020, 10 pages.

International Search Report and Written Opinion in PCT/EP2019/087056; dated Feb. 17, 2020, 13 pages.

Abramson D et al. Lactate clearance and survival following injury. J. Trauma. 1993, 35: 584-8.

ADVANZ Pharma, Liothyronine Sodium 20 micrograms Powder for Solution for Injection, www.medicines.org.uk/emc/product/2805/smpc#gref, Aug. 10, 2007, 7 pages.

Anonymous, "Triiodothyronine for the Treatment of Critically Ill Patients With COVID-19 Infection", Internet Apr. 16, 2020 (Apr. 16, 2020), pp. 1-10.

Cho, Y.I., et al., Hemorheology and microvascular disorders, Korean Circ. J., Jun. 2011; 41(6): 287-95.

Clinical Trial Results: Triiodothyronine for the treatment of critically ill patients with COVID-19 infection (Thy-Support Study), EudraCT: 2020-001623-13.

Dekker Nam, et al. Microvascular Alterations During Cardiac Surgery Using a Heparin or Phosphorylcholine-Coated Circuit. J. Cardiothorac. Vasc. Anesth. 2020, 34 (4): 912-919.

Dekker Nam, et al. Postoperative microcirculatory perfusion and endothelial glycocalyx shedding following cardiac surgery with cardiopulmonary bypass, Anesthesia, 2019, 74: 609-618.

First Office Action in CN Patent Application No. 202180029865.9 dated Nov. 24, 2023.

Gore, Dennis C. et al., Triiodothyronine (T3) Administration in Patients with Sepsis Induced Euthyroid Sick Syndrome: Hemodynamic and Metabolic Effects, Sepsis, 1988, pp. 163-169.

Harisson, M., Erythrocyte sedimentation rate and C-reactive protein, Aust. Prescr. 2015, 38 (3): 93-4.

ICSH recommendations for measurement of erythrocyte sedimentation rate, J. Clin. Pathol. 1993, 46 (3): 198-203.

Iervasi, et al., Thyroid and Heart, A Comprehensive Translational Essay, Second Edition, Springer Nature Switzerland, 2020, 429 pages.

Iliopulou, et al., Time-dependent and independent effects of thyroid hormone administration following myocardial infarction in rats, Molecular Medicine Reports, Mar. 12, 2018, 18:864-876.

International Search Report and Written Opinion in related PCT/GR2021/000019; dated Aug. 9, 2021, 9 pages.

Iordaniss Mourouzis et al., "Triiodothyronine prevents tissue hypoxia in experimental sepsis: potential therapeutic implications", Intensive Care Medicine Experimental, Biomed Central Ltd, London, UK, vol. 9, No. 1, Apr. 9, 2021 (Apr. 9, 2021), pp. 1-4.

Kaptein, EM, et al., Thyroid hormone therapy for postoperative nonthyroidal diseases: a systematic review and synthesis. J. Clin. Endocrinol. Metab. 2010, 95: 4526-4534.

Klouwenberg, PK. Classification of sepsis, severe sepsis and septic shock: the impact of minor variations in data capture and definition of SIRS criteria. Intensive Care Med 2012, 38, pp. 811-819.

(56)        References Cited

OTHER PUBLICATIONS

Lapic, I, et al., Erythrocyte sedimentation rate is associated with severe coronavirus disease 2019 (COVID-19): a pooled analysis, Clin. Chem. Lab Med., 2020, 58(7): 1146-1148.

Lelubre Christophe et al., "Mechanisms and treatment of organ failure in sepsis", Apr. 24, 2018 (Apr. 24, 2018), vol. 14, No. 7, pp. 417-427.

Li, et al., Thyroid Hormone Protects Primary Cortical Neurons Exposed to Hypoxia by Reducing DNA Methylation and Apoptosis, Endocrinology, Oct. 1, 2019; 160(10):2243-2256.

Lourbopoulos, et al., Effects of Thyroid Hormone on Tissue Hypoxia: Relevance to Sepsis Therapy, Journal of Clinical Medicine, 2021, 10, 5855,18 pages.

Ma, Shwu-Fan, et al., Type 2 Deiodinase and Host Responses of Sepsis and Acute Lung Injury Am. J. of Respir. Cell Mol. Biol., 2011, 45 (6): 1203-1211.

Maiden, Matthew; Tri-iodothyronine (T3)Therapy in a Pre-Clinical Model of Septic Shock, A thesis submitted for the degree of Doctor of Philosophy, Adelaide Research & Scholarship, Mar. 23, 2015, 306 pages.

Maillet JM et al. Frequency, risk factors, and outcome of hyperlactatemia after cardiac surgery. Chest 2003, 123: 1361-6.

Manolis, et al., Cardiovascular Complications of the Coronavirus (COVID-19) Infection, ResearchGate, Rhythmos, vol. 15, No. 2, Apr. 7, 2020, 7 pages.

Mantzouratou, et al., Thyroid Hormone and Heart Failure: Charting Known Pathways for Cardiac Repair/ Regeneration, Biomedicines, Mar. 21, 2023, 11, 975, pp. 1-13.

Mourouzis, et al., Effects of T3 Administration on Ex Vivo Rat Hearts Subjected to Normothermic Perfusion: Therapeutic Implications in Donor Heart Preservation and Repair, Transplant International, Feb. 7, 2023, vol. 36 | Article 10742, pp. 1-10.

Mourouzis, et al., The Potential of Thyroid Hormone Therapy in Severe COVID-19: Rationale and Preliminary Evidence, International Journal of Environmental Research and Public Health, Jun. 30, 2022, 19, 8063, pp. 1-13.

Muz et al. The role of hypoxia in cancer progression, angiogenesis, metastasis, and resistance to therapy. Hypoxia 2015, 3: 83-92.

Nair, A.B. and Jacob, S., A simple practice guide for dose conversion between animals and humans, J. Basic Clin. Pharma, 2016, 7: 27-31.

Newby, L. Kristin, et al., Losmapimod, a novel p38 mitogen-activated protein kinase inhibitor, in non-ST-segment elevation myocardial infarction: a randomised phase 2 trial, Lancet (2014) 384, 1187-95.

Nguyen, HB et al. Early lactate clearance is associated with biomarkers of inflammation, coagulation, apoptosis, organ dysfunction and mortality in severe sepsis and septic shock. J. Inflam. 2010, 7: 6.

Nuzzo, E., et al., Pyruvate dehydrogenase levels are low in sepsis. Crit Care, 2015, 19: P33 p. 11.

O'Brien J.M., et al., Sepsis, Am. J. Med. 2007, 120, pp. 1012-1022.

Office Action received for Japanese Patent Application No. 2022-563957, mailed on Mar. 25, 2025, 6 pages (3 pages of English Translation and 3 pages of Original Document).

Office Action received for Korean Patent Application No. 10-2022-7039203, mailed on Feb. 19, 2026, 14 pages (7 pages of English Translation and 7 pages of Original Document).

Özozan, et al., Is tri-iodothyronine a better choice than activated protein C in sepsis treatment?, Ulus Travma Acil Cerrahi Derg, Nov. 2019, vol. 25, No. 6, p. 545-554.

Padhi, R., et al., Prognostic significance of nonthyroidal disease syndrome in critically ill adult patients with sepsis. Int. J. Crit. Illn. Inj. Sci. 2018, 8: 165-172.

Pantos, C., et al., Thyroid hormone improves postischaemic recovery of function while limiting apoptosis: a new therapeutic approach to support hemodynamics in the setting of ischaemia-reperfusion? Basic Res. Cardiol. (2009) 104, 69-77; doi:10.1007/s00395-008-0758-4.

Pantos, et al., Acute triiodothyronine treatment and red blood cell sedimentation rate (ESR) in critically ill COVID-19 patients: A novel association?, Clinical Hemorheology and Microcirculation 79 (2021) pp. 485-488.

Pantos, et al., Effects of Acute Triiodothyronine Treatment in Patients with Anterior Myocardial Infarction Undergoing Primary Angioplasty: Evidence from a Pilot Randomized Clinical Trial (ThyRepair Study), THYROID, vol. 32, No. 6, 2022, @ Mary Ann Liebert, Inc., DOI: 10. 1089/thy.2021.0596, pp. 714-724.

Pantos, et al., Thyroid hormone receptor a1 as a novel therapeutic target for tissue repair, Ann Transl Med, Jun. 12, 2018, 11 pages.

Pantos, et al., Triiodothyronine for the treatment of critically ill patients with COVID-19 infection: A structured summary of a study protocol for a randomised controlled trial, Trials 21, Article No. 573, Jun. 26, 2020, 3 pages.

Pantos, et al., Use of triiodothyronine to treat critically ill COVID-19 patients: a new clinical trial, Critical Care, Apr. 30, 2020, 24:209, 2 pages.

Petrov V.S., et al., Extracorporeal haemocorrection and its impact on free-radical oxidation and antioxidant defense in abdominal sepsis. Messenger of Anesthesiology and Resuscitation, 2018, vol. 15, No. 1, p. 40-45.

Reems, M.M., et al., Central venous pressure: principles, measurement, and interpretation. Compend. Contin. Educ. Vet. 2012, 34(1):E1.

Renoux, et al., Impact of COVID-19 on red blood cell rheology, Clinical Trial, British Journal of Haematology and John Wiley & Sons Ltd., Jan. 7, 2021, 192, 4 pages.

Rudski, L.G., et al., Guidelines for the echocardiographic assessment of the right heart in adults: a report from the American Society of Echocardiography endorsed by the European Association of Echocardiography, a registered branch of the European Society of Cardiology, and the Canadian Society of Echocardiography, J. Am. Soc. Echocardiogr. 2010, 23: 685-713.

Sakr Y, et al. Persistent microcirculatory alterations are associated with organ failure and death in patients with septic shock. Crit. Care Med. 2004, 32 (9): 1825-31.

Triiodothyronine for the Treatment of Critcally Ill Patients with COVID-19 Infection, ClinicalTrials.gov, Uni-Pharma Kleon Tsetis Pharmaceutical Laboratories S.A., 2020, pp. 1-2.

Makino, A. et al., Thyroid Hormone Recepton-B Is Associated with Coronary Angiogenesis during Pathological Cardiac Hypertrophy, The Endocrine Society, Endocrinology, Apr. 2009, pp. 2008-2015.

Notification of Reasons for Refusal in JP Patent Application No. 2022563957 dated Feb. 16, 2026.

Uni-Pharma Kleon Tsetis Pharmaceutical Laboratories S.A., Triiodothyronine for the Treatment of Critically Ill Patients with COVID-19 Infection (Thy-Support), ClimincalTrials.gov, Identifier: NCT04348513, Apr. 16, 2020, 10 pages.

Vergote, I., et al., A randomized, double-blind, placebo-controlled phase 1b/2 study of ralimetinib, a p38 MAPK inhibitor, plus gemcitabine and carboplatin versus gemcitabine and carboplatin for women with recurrent platinum-sensitive ovarian cancer, Gynecologic Oncology, https://doi.org/10.1016/j.ygyno.2019.11.006., (2019), 9 pages.

Visveswaran Gautam K Et Al, "Acute left ventricular dysfunction complicating pregnancy on ECMO: Tri-iodothyronine to the rescue with real time transesophageal echocardiography", Journal of Cardiology Cases, Elsevier, Amsterdam, NL Vol. 13, No. 1, Nov. 3, 2015 (Nov. 3, 2015), pp. 33-36.

Yokoe, T., et al., Triiodothyronine (T3) ameliorates the cytokine storm in rats with sepsis. Crit. Care 2000, 4: P59; pp. 35.

* cited by examiner

Incidence of MVO > 0.47%- CMR

EF% 6months [CMR]

LV volumes [ml/m$^2$] 6 months

L-TRIIODOTHYRONINE (T3) FOR USE IN LIMITING MICROVASCULAR OBSTRUCTION

The present invention concerns a novel treatment and treatment regimen after a successful Primary Percutaneous Coronary Intervention (PPCI), in the course of an acute ST-segment-elevation myocardial infarction (STEMI), with a view to limit or prevent the occurrence of Microvascular Obstruction (MVO).

STEMI is initiated by occlusion of a large epicardial coronary artery due to atherosclerotic disease. A successful PPCI restores blood flow in the occluded coronary artery. However, during the reperfusion an obstruction can occur at the level of small vessels, a phenomenon known as MVO, and thus blood flow may not be restored in all myocardium despite successful PPCI on large vessels. MVO is a prevailing and common complication after PPCI for STEMI patients and is associated with larger infarct size, poor recovery of ventricular function and reduced survival.

Acute myocardial infarction is a common cause of patients increased mortality and morbidity. Prompt restoration of blood flow in the occluded epicardial coronary artery by primary percutaneous coronary intervention (PPCI), after an acute ST-segment-elevation myocardial infarction (STEMI), is currently the most effective therapy for reducing myocardial infarct size and preserving left ventricular systolic function. However, mortality and morbidity remain significant. Current evidence suggests that this is mainly attributed to the development of microvascular obstruction (MVO), and is associated with adverse left ventricular remodeling and worse clinical outcomes. The gold standard for diagnosis of MVO is contrast-enhanced cardiac magnetic resonance within 14 days after STEMI. MVO can be quantified in each patient as the percentage of left ventricular (LV) myocardium that is not adequately perfused despite restoration of blood flow in the occluded large coronary artery. MVO can be also assessed with cine coronary angiography, incomplete resolution of ST segment elevation measured on electrocardiogramd myocardial contrast echocardiography. To date, there is no effective therapy to prevent or minimize the burden of MVO and is currently considered irreversible.

The phenomenon of MVO refers to the inability to reperfuse a previously ischemic myocardium in the presence of a patent epicardial coronary artery. MVO occurs in almost half of STEMI patients after PPCI and is associated with worse outcomes, independent of the infarct size (J Thorac Dis. 2018 March; 10(3):1343-1346). In a meta-analysis of 1025 STEMI patients reperfused by PPCI and with a CMR performed within the first week, MVO was associated with the occurrence of a composite of cardiac death, congestive heart failure, and myocardial reinfarction with a hazard ratio of 3.74, whereas Myocardial Infarction (MI) size was not, in a multivariate Cox regression analysis, after adjusting for confounders. In a more recent meta-analysis using individual patient data from seven randomized primary PCI trials (n=1688 patients), MVO was assessed within 7 days after reperfusion by CMR using late gadolinium enhancement imaging (Eur Heart J. 2017 Dec. 14; 38(47):3502-3510). Patients were analyzed using as a cut-off point for MVO the value of 0.47%, which was the median value (50% of patients were below and 50% were above this value). Increased hazard ratio for the 1-year composite endpoint of all-cause mortality or heart failure hospitalization was found in patients with large extent of MVO (above the median of 0.47%). This effect was independent from infarct size, age, gender, smoking status and the existence of hypertension, hyperlipidemia and diabetes.

Despite having a patent epicardial coronary artery post-PPCI, those patients with MVO have areas of ongoing hypoperfusion at the microcirculation level. Therapeutic approaches that could theoretically reduce MVO by achieving patency of the microcirculation, have failed. Remarkably, important advances in PCI techniques (such as aspiration thrombectomy or deferred stenting strategy) have had limited impact on the incidence of MVO and related outcomes [J Thorac Dis 2018; 10(3):1343-1346]. Recently, high-dose intracoronary adenosine and sodium nitroprusside failed to reduce MVO and MI size in a cohort of 247 reperfused STEMI patients [Eur Heart J. 2016; 37:1910-1919.] Some experimental studies demonstrated that the initiation of therapeutic hypothermia minutes after restoring flow in a proximally-occluded coronary artery significantly reduced the incidence of no-reflow, but did not affect infarct size.

In summary, there are no effective treatments for MVO in STEMI patients available. Thus, research validating novel therapies in this arena is urgently needed. In this context, the present invention refers to a novel effect of L-triiodothyronine (T3) on limiting microvascular obstruction after PPCI in STEMI patients.

However, to date administration of thyroid hormones (TH) in all possible situations involving acute myocardial infarction is avoided due to long held belief that TH may be detrimental for the ischemic myocardium. A strong prejudice exists among clinicians to consider even the restoration of TH levels to normal in hypothyroid patients with acute myocardial infarction. In fact, the current belief is that the use of TH in this setting can increase heart rate which results in enhanced oxygen consumption and energy expenditure and thus, could result in worsening of myocardial injury and infarct size. Furthermore, high levels of TH have been related to increased incidence of arrhythmias which is one of the causes of early mortality in these patients. In this regard, early clinical studies, such as the Coronary Drug Project in 1970s, have shown that long-term administration of high doses D-thyroxine in patients after acute myocardial infarction resulted in increased mortality. These data have resulted in very cautious use of TH in patients with coronary artery disease (CAD) in general. However, strong epidemiological data showing that stress induced low T3 is associated with worse outcomes in patients with CAD, has revived research interest in the field. According to this evidence, several experimental studies were conducted to investigate the efficacy of long-term TH replacement therapy in restoring cardiac function in animals with experimental myocardial infarction. Treatment with near physiological doses of TH was shown to favorably remodel the postischemic myocardium with favorable changes in myosin heavy chain (MHC) expression pattern (less B-MHC and increased a-MHC), ellipsoid reshaping and improved left ventricular ejection fraction. Interestingly, in a mouse model of myocardial infarction, TH replacement therapy restored recovery of function while long-term treatment with high doses of TH resulted in increased mortality (Ann Transl Med. 2018 June; 6(12):254).

Documents US2011/0142947A1 and US2005/0059574A1 refer to T3 compositions suitable for use in cardiac arrest, cardiac arrest with cardiac electrical standstill, cardiogenic shock and acute heart failure. These pathological entities are distinct from myocardial infarction or myocardial ischemia and reperfusion. In fact, a small portion of patients with STEMI (5-10%) may present with cardiac arrest, cardiogenic shock and acute heart failure.

Documents WO 95/00135 and Mdzinarishvili A. in *Drug Deliv. and Transl. Res.* (2013) 3:309-317, refer to the use of T3 in central nervous system ischemia and ischemic brain stroke. These pathological entities are entirely distinct from MI or myocardial ischemia and reperfusion and in this context are completely out of the scope of the current invention.

Document WO 02/051403 refers to the value of measuring T3 levels in blood as a biomarker to evaluate prognosis in patients with myocardial infarction (indicator for mortality). However, especially Example 1 refers to reverse T3 (rT3) which is a different molecule compared to T3, in particular, the missing de-iodinated iodine is from the inner ring of the thyroxine molecule compared with outer ring on T3. Due to this fact reverse T3 is inactive.

The potential of TH replacement therapy in patients with acute myocardial infarction (AMI) has been tested in a recent phase II clinical trial (THIRST study-EudraCT: 2009-010869-23). In this randomized controlled trial of oral T3 in 37 patients with STEMI and low serum FT3 levels, T3 replacement therapy for 6 months was shown to be safe and effective in reducing regional cardiac dysfunction. Left ventricular ejection fraction and myocardial infarct size, as assessed by cardiac MRI, did not show any benefit. In this trial, T3 was commenced 72 h after the onset of STEMI, and the preparation was administered three times per day (maximum dosage 15 $\mu$g/m$^2$/day). This small trial provides evidence that normalization of serum T3 levels in patients with STEMI who have low circulating T3 levels is safe, if T3 therapy is commenced a few days after the acute event.

The potential effect of early administration of high dose TH (acute treatment) after an index event has been also investigated in experimental models of ischemia-reperfusion (I/R) using isolated rat heart preparations. Thus, high dose T3 (triiodothyronine) administration at the onset of reperfusion resulted in enhanced post-ischemic recovery of function and less myocardial injury as indicated by apoptosis. In this ex vivo experimental setting, T4 (L-thyroxine) was shown to have no effect on myocardial injury (Heart Fail Rev. 2015 May; 20(3):273-82). Based on this evidence, a phase II study (Thy-REPAIR-EudraCT: 2016-000631-40) was designed to translate these results in clinical practice. Thy-REPAIR explores the effects of high-dose T3 treatment intravenously starting immediately after reperfusion and continuing for 48 hours in patients with anterior or anterolateral STEMI undergoing primary PCI. This is a double-blind randomized trial. The primary end point of this study is recovery of myocardial function after 6 months of the index event as this is assessed by Cardiac Magnetic Resonance (CMR) at discharge and at 6 months after acute myocardial infarction. This study also explores the potential effects of T3 treatment on infarct size and cardiac remodeling by assessing changes in LV volumes and geometry.

In the course of this study certain observations were made that led to the present invention.

The invention in particular concerns L-triiodothyronine for use in the treatment as set forth in the appending claims. In the broader sense, the present invention concerns L-triiodothyronine for use in the treatment of microvascular obstruction. Treatment of MVO in this context relates to the lessening of microvascular obstruction in comparison to patients which were not supplied with T3. MVO may be determined on the basis of both Cardiac Magnetic Resonance (CMR) imaging, being performed 7-12 days following primary percutaneous coronary intervention (PPCI) and restoration of ST elevation in electrocardiogram (ECG). Infarct size and ejection fraction was measured by CMR. Infarct size was also assessed enzymatically by measuring levels of troponin in blood.

The present invention in particular concerns a medicament comprising triiodothyronine (T3) administered to ST-elevation myocardial infarction patients that undergo primary percutaneous coronary intervention (PPCI).

The present invention in particular concerns use of a T3 solution that is administered intravenously as a solution with a concentration of T3 in the range of 5 to 20 $\mu$g/ml, in particular 10 $\mu$g/ml.

Typically, the treatment is commenced with the administration of a relative high dose after reperfusion. This bolus may be in the range of 0.7 $\mu$g/kg to 0.9 $\mu$g/kg. Thus, with a T3 solution comprising 10 $\mu$g L-triiodothyronine in 1 ml solution, patients may receive a bolus administration over 2-3 min of in between 4.0 and 8.0 ml.

This bolus may be administered intravenously.

Subsequent to the high-dose bolus, the patients receive a continued infusion over 24-72 hours. Typically, the patients receive a continuous injection of T3 in the range of 0.1 to 0.2 $\mu$g/kg/h.

These doses are considered much higher than in the normal treatment of patients with non-adequate thyroid functions (e.g. patients with hypothyroidism or myxedema). Accordingly, and in the course of a treatment over about 48 h, a patient in the weight range of 60 kg to 100 kg, may receive in total 350 to 600 $\mu$g T3. This dose is 8-12 times higher compared to the dose used in the Thirst trial to restore T3 levels to normal range.

Figure 11:
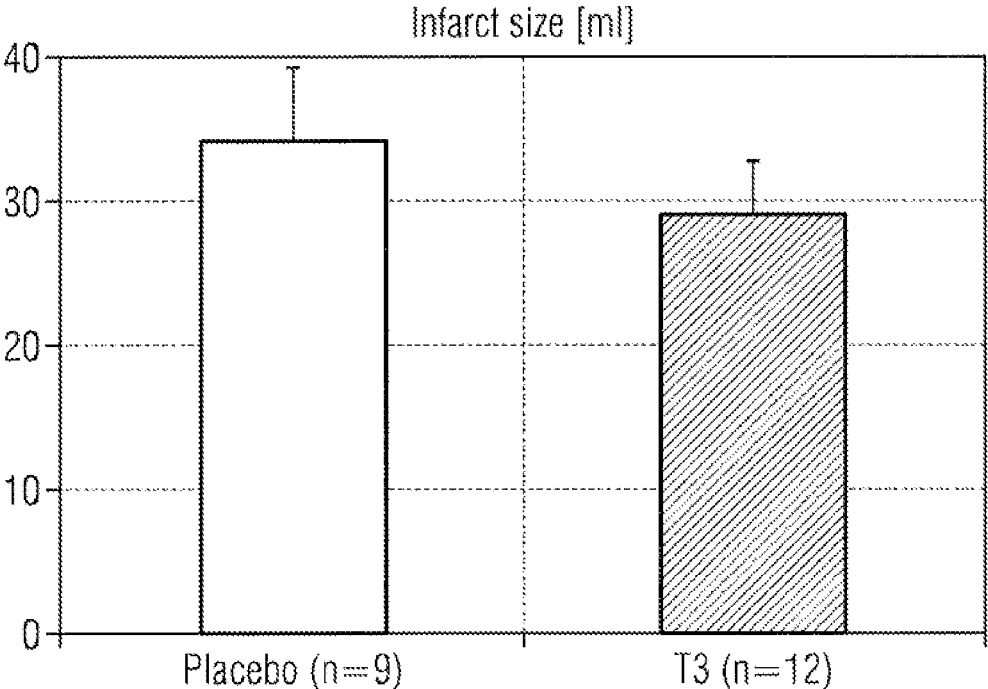

5 group. Cardiac function is not related to the extent of injury indicating a different pathophysiological process FIG. 11: CMR analysis shows no difference in infarct size (extent of injury) between placebo and T3 group FIG. 12: Left ventricular ejection fraction assessed by echocardiography at different time points in STEMI patients treated with placebo and T3

Figure 13:
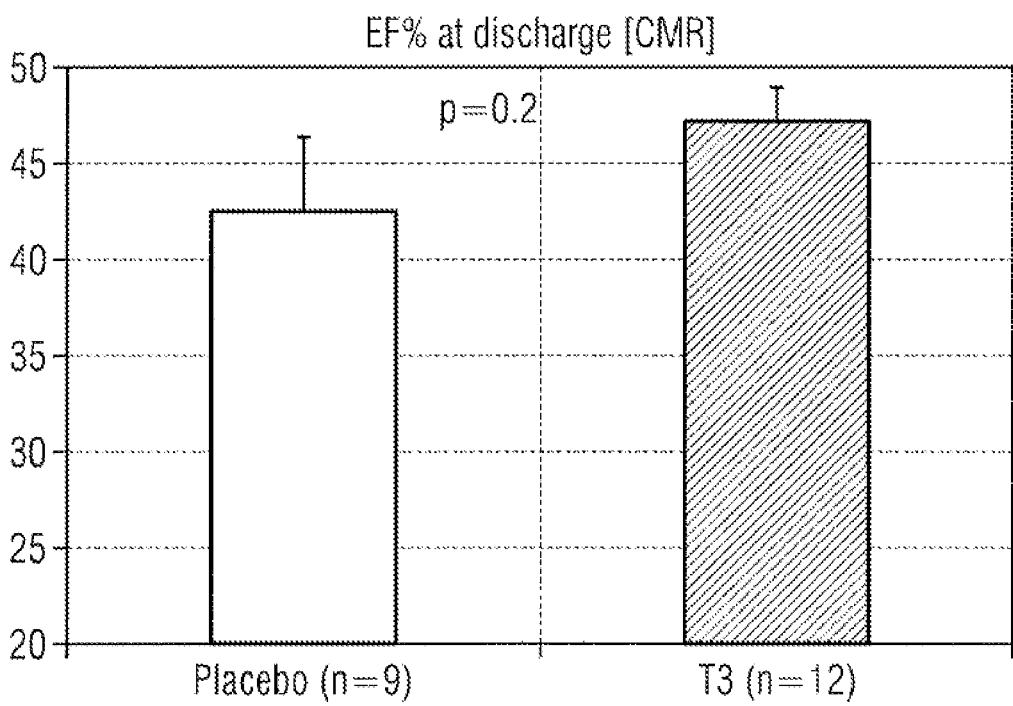
Figure 13:
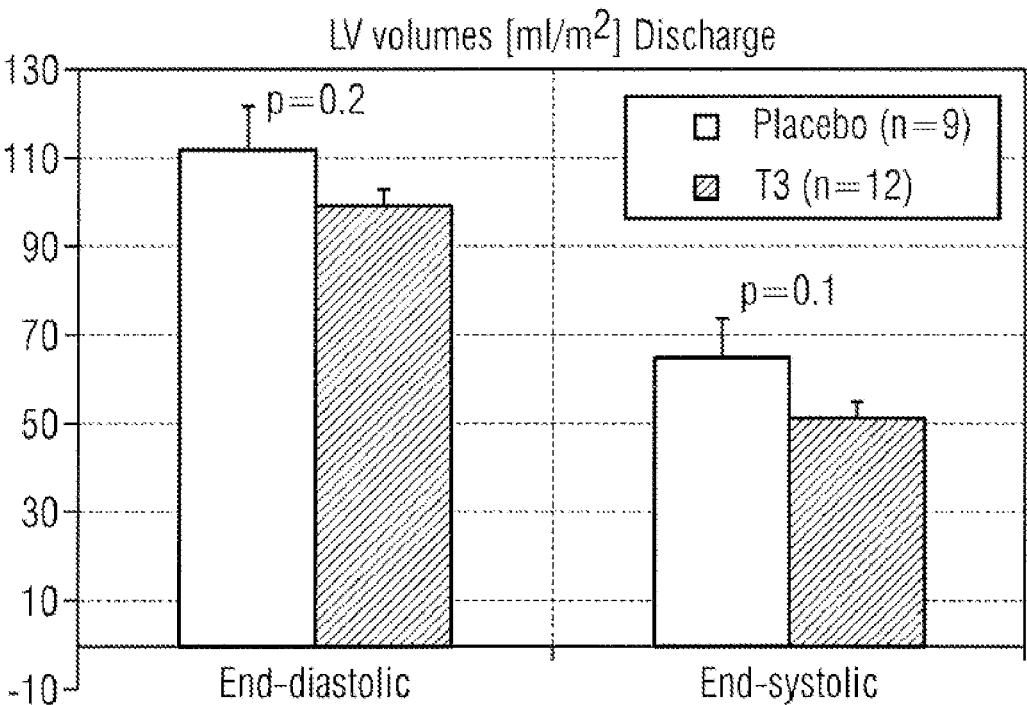

FIG. 13: Left ventricular ejection fraction and left ventricular end-diastolic (LVEDVi) and end-systolic (LVEDVi) volumes assessed by Cardiac Magnetic Resonance at discharge in STEMI patients treated with placebo and T3

Figure 14:
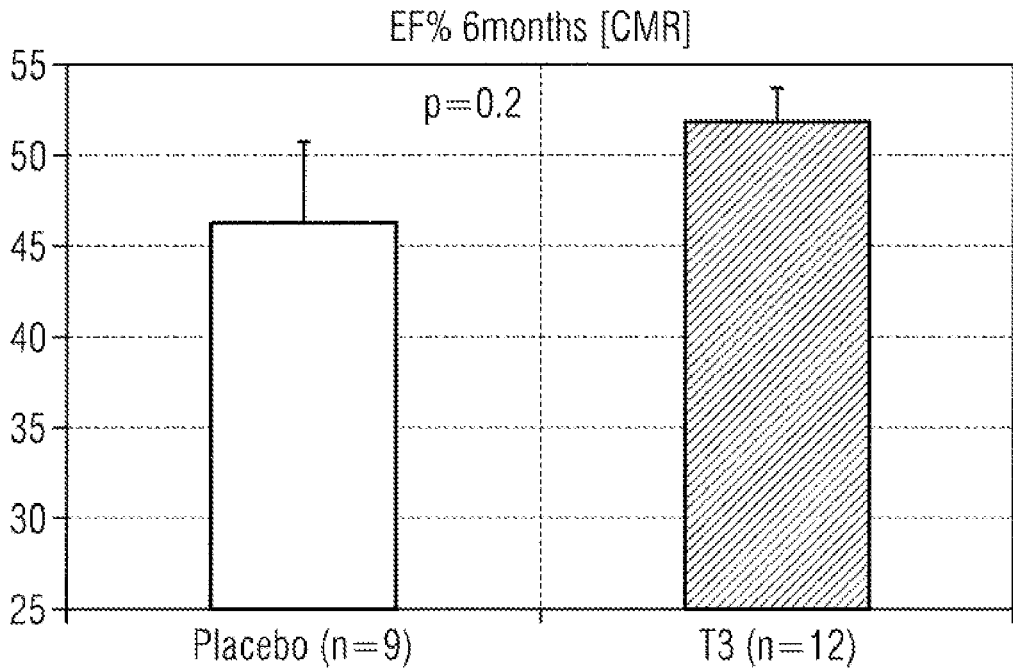
Figure 14:
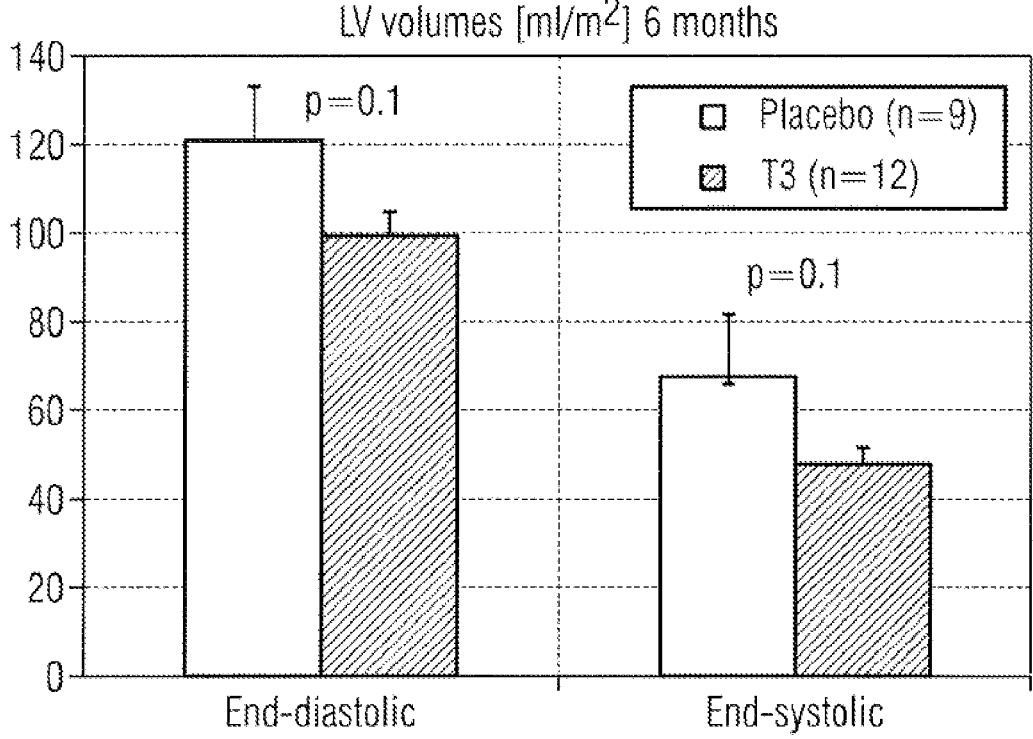

FIG. 14: Left ventricular ejection fraction and left ventricular end-diastolic (LVEDVi) and end-systolic (LVEDVi) volumes assessed by Cardiac Magnetic Resonance at 6 months in STEMI patients treated with placebo and T3

A practitioner may consult the following explanation and tables, which show a dosage schedule of T3 administration according to the patient's weight.

TABLE 1

Dosage schedules of T3 Solution for injection 10 µg/ ml according to patient's weight

| Patient's weight | Bolus administration over 2-3 min | Continuous infusion per 24 hours (pump rate 10.4 mL/h) |
|---|---|---|
| 62 Kg (min) | 5.0 ml (50 µg T3) | 17 ml (170 µg T3) in 233 ml NaCl 0.9% |
| 66 Kg | 5.5 ml (55 µg T3) | 18 ml (180 µg T3) in 232 ml NaCl 0.9% |
| 70 Kg | 5.5 ml (55 µg T3) | 19 ml (190 µg T3) in 231 ml NaCl 0.9% |
| 74 Kg | 6 ml (60 µg T3) | 20 ml (200 µg T3) in 230 ml NaCl 0.9% |
| 77 Kg | 6 ml (60 µg T3) | 21 ml (210 µg T3) in 229 ml NaCl 0.9% |
| 81 Kg | 6.5 ml (65 µg T3) | 22 ml (220 µg T3) in 228 ml NaCl 0.9% |
| 85 Kg | 7.0 ml (70 µg T3) | 23 ml (230 µg T3) in 227 ml NaCl 0.9% |
| 89 Kg | 7.0 ml (70 µg T3) | 24 ml (240 µg T3) in 226 ml NaCl 0.9% |
| 92 Kg | 7.5 ml (75 µg T3) | 25 ml (250 µg T3) in 225 ml NaCl 0.9% |
| >95 Kg (max) | 7.5 ml (75 µg T3) | 26 ml (260 µg T3) in 224 ml NaCl 0.9% |

As a further example, the practitioner may consider the following.

For a patient of 77 Kg of weight, a dose of 6 ml of T3 Solution for injection 10 µg/ml (total of 60 µg T3) is administered intravenously as a bolus over 2-3 min, upon the beginning of reperfusion during primary PCI. Subsequently and for the next 24 hours, the patient receives a solution comprising of 21 ml of T3 Solution for injection 10 µg/ml (total of 210 µg of T3) diluted in 229 ml of NaCl 0.9%, which are administered in the aid of a pump at a steady flow rate of 10.4 ml/h. The last step repeated for another 24 hours, thus the total amount of T3 administered to the patient from the beginning of the treatment is 480 µg. Table 2 summarizes the total amount of T3 administered to each patient from the beginning of the treatment.

TABLE 2

Total amount of T3 administered to each patient after treatment for 48 h

| Patient's weight | Total Dose of T3 during the 48 hours period of administration |
|---|---|
| 62 Kg (min) | 390 µg |
| 66 Kg | 415 µg |
| 70 Kg | 435 µg |
| 74 Kg | 460 µg |
| 77 Kg | 480 µg |

6

TABLE 2-continued

Total amount of T3 administered to each patient after treatment for 48 h

| Patient's weight | Total Dose of T3 during the 48 hours period of administration |
|---|---|
| 81 Kg | 505 µg |
| 85 Kg | 530 µg |
| 89 Kg | 550 µg |
| 92 Kg | 575 µg |
| >95 Kg (maximum) | 575 µg |

Apparently, the present invention is based on the surprising observation that with the dosage regimen as considered in the present invention (high-dose of T3 above any consideration of a thyroid replacement therapy) the extent of microvascular obstruction (MVO) is lowered. MVO after reperfusion is now recognized as an important prognostic factor of survival in these patients independent from infarct size. Thus, any reduction of MVO can reduce the mortality rate of STEMI patients, which undergo treatment with PCI.

Triiodothyronine in the study is used in the form of a T3® Solution for injection 10 µg/ml that contains 150 µg of L-triiodothyronine in a total volume of 15 ml per vial. The medicament is a clear, colorless solution containing the active substance Liothyronine sodium and other ingredients including dextran 70, NaOH 1 N and water for injection. Liothyronine sodium is synthesized in vitro. The medicament could also be supplied in the lyophilized form and reconstituted with water for injection or saline immediately prior to use.

Example 1

| No | Name of ingredient(s) | Quantity/1 ml |
|---|---|---|
| | Active ingredient: | |
| 1. | Liothyronine sodium | 10.0 µg |
| | Other ingredient (s): | |
| 1. | Dextran 70 | 60.0 mg |
| 2. | NaOH 1N | q.s. pH 10 |
| 3. | Water for Injections | qs 1.0 |

Figure 1:
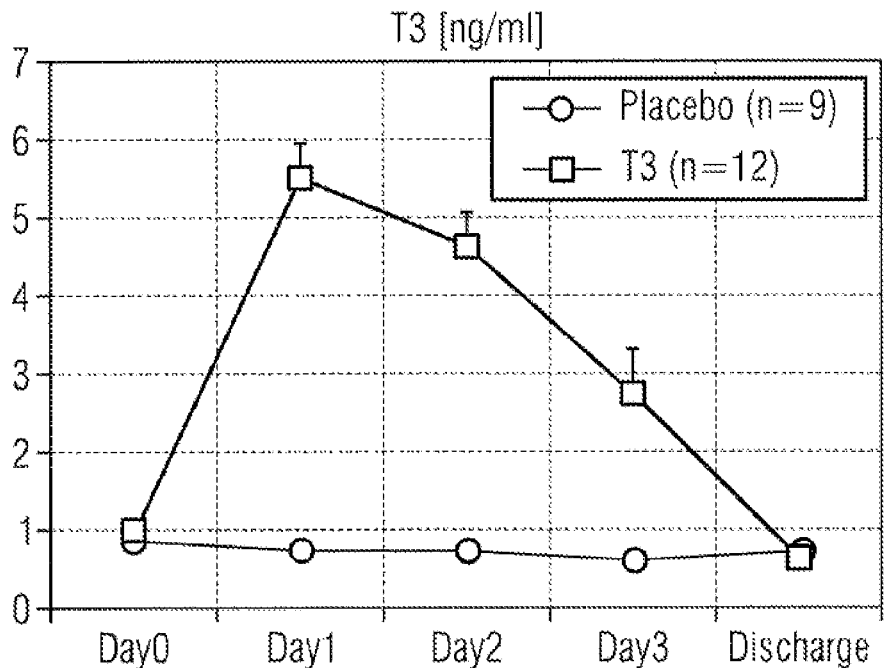
FIG. 1: Levels of triiodothyronine in serum during hospitalization in patients after acute myocardial infarction treated with placebo and T3

The dose administered is 0.8 µg/kg intravenously bolus starting immediately after successful opening of the culprit vessel has been established in the hemodynamic lab and followed by an infusion of 0.113 µg/kg/h intravenously for 48 hours. Administration of the medicament increases significantly the levels of T3 in serum at 24 and 48 hours (5.5 (0.5) ng/ml and 4.5 (0.5) ng/ml respectively compared to 0.79 (0.06) and 0.76 (0.06) ng/ml for the placebo group, p<0.01). This treatment increases T3 levels in serum far above normal range for 72 hours and allows return to normal at discharge (7th day) (FIG. 1).

Figure 2:
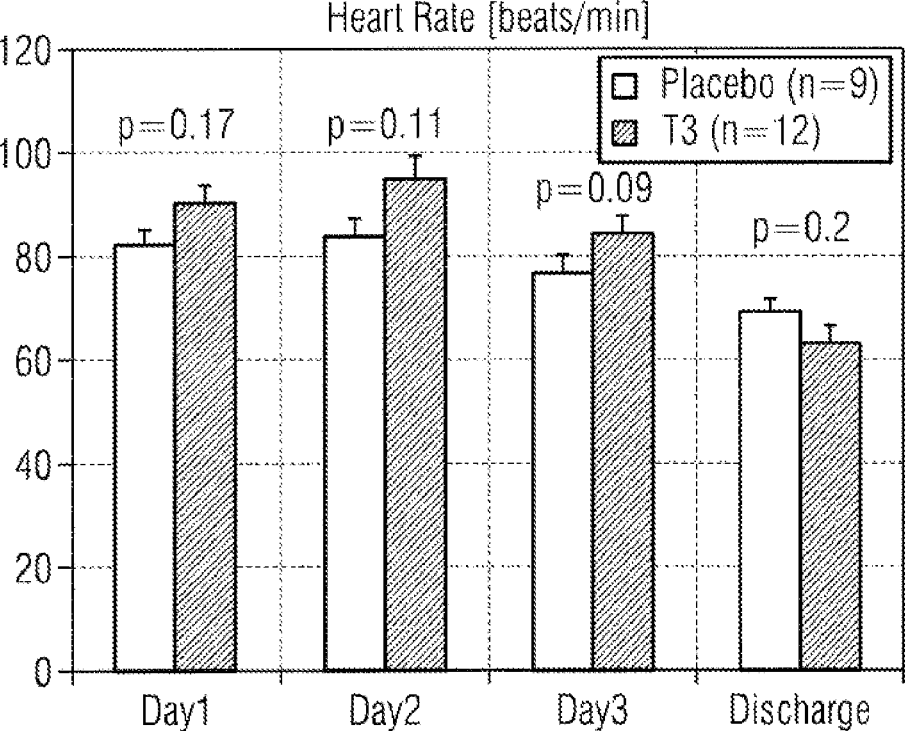
FIG. 2: Heart rate assessed during hospitalization in STEMI patients treated with placebo and T3
Figure 3:
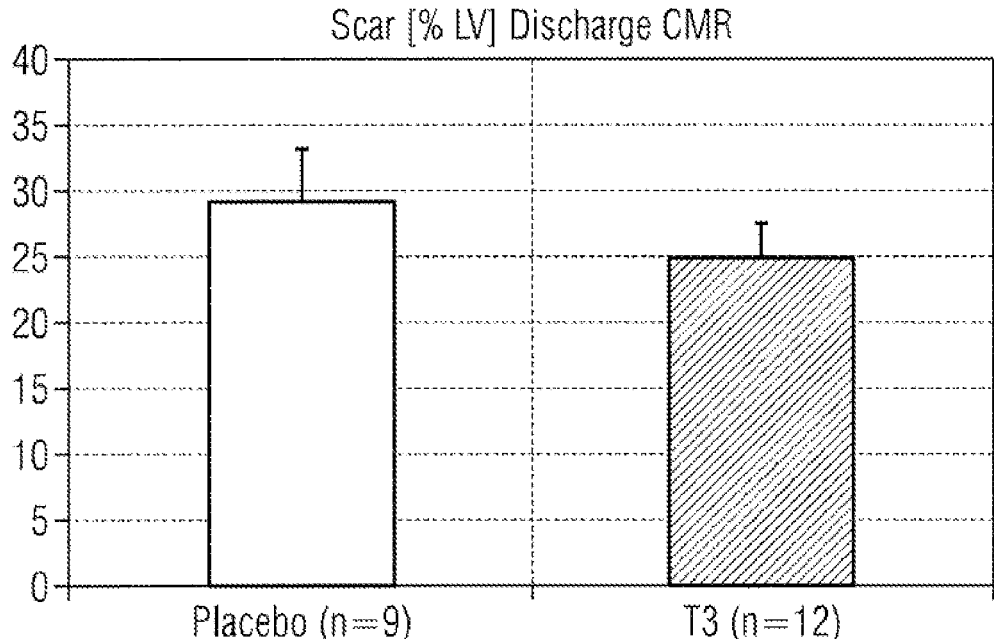
FIG. 3: Extent of scar as percentage of the Left ventricle (LV) assessed by Cardiac Magnetic Resonance at discharge in STEMI patients treated with placebo and T3

Administration of high dose T3 resulted in a non-significant increase in heart rate during the first 3 days (FIG. 2). Despite the possible increase in oxygen consumption, no increase in infarct size (IS) is found with T3 in contrast to the current belief (FIG. 3).

Beyond our expectations, an important and surprising finding of the present study was revealed from the routine analysis of contrast-enhanced cardiac magnetic resonance which involves the determination of mean microvascular obstruction and the incidence of microvascular obstruction in these patients. Actually, cardiac magnetic resonance with gadolinium represents the gold-standard method for detection of MVO in patients with STEMI. MVO can be quantified in each patient as the percentage of left ventricular (LV) myocardium that is not adequately perfused despite restoration of blood flow in the occluded large coronary artery.

Figure 4:
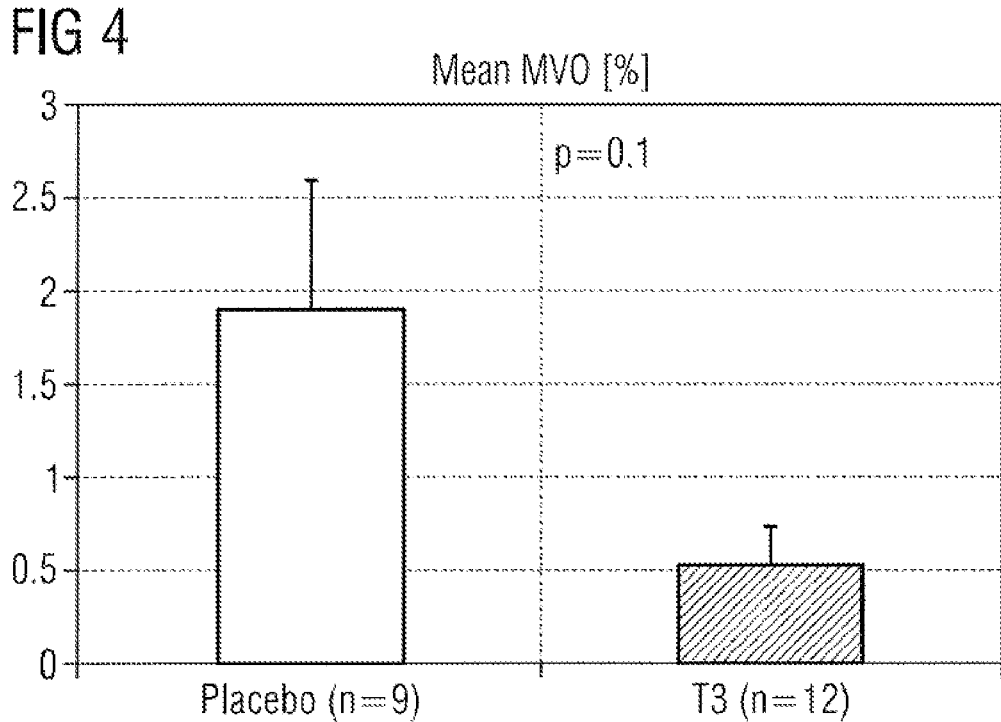
FIG. 4: Mean MVO assessed by Cardiac Magnetic Resonance at discharge in STEMI patients treated with placebo and T3

In fact, the extent of mean microvascular obstruction was less in the T3 treated STEMI patients based on CMR data at discharge (7-12 days after the event) (FIG. 4).

Figure 5:
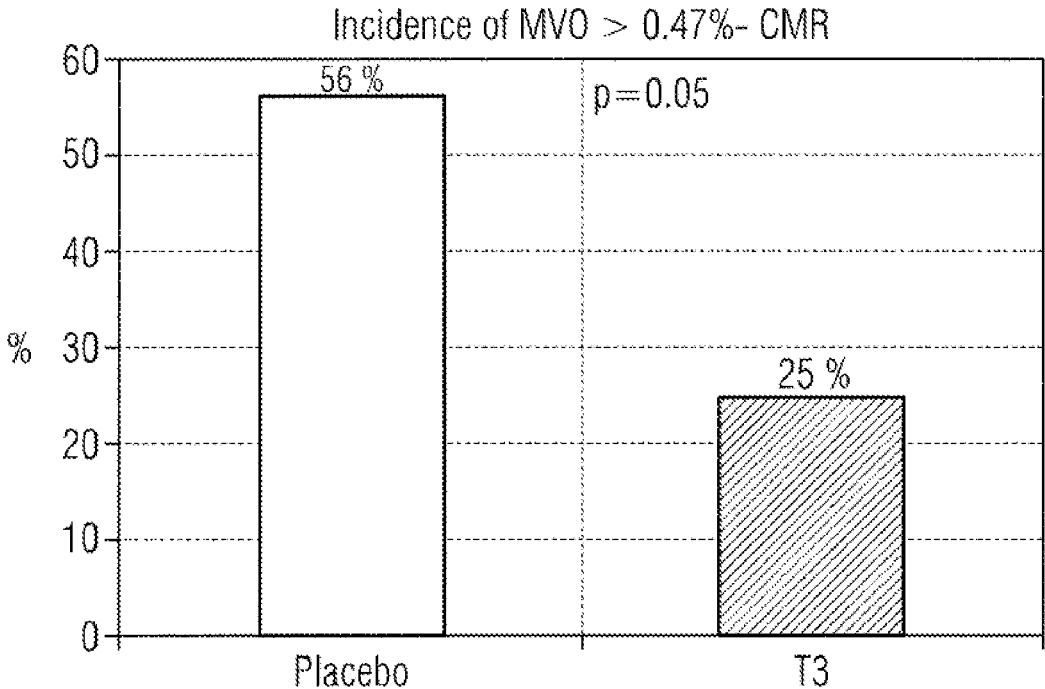
FIG. 5: Percentage of patients with large extent of MVO in placebo and T3 treated group. T3 significantly reduces the percent of patients with large extent of MVO

The incidence of MVO was assessed using the value of 0.47% as a cut-off point for patients with large and small extent of MVO as previously described. This analysis was additionally performed and provides a strong evidence about the T3 effect on MVO. In the placebo group (n=9), a large extent of MVO was found in 56% of patients consistent with previous published reports in the literature. Surprisingly, in the T3 treated group (n=12), a large extent of MVO was found only in 25% of patients, p=0.05 (FIG. 5).

Figure 6:
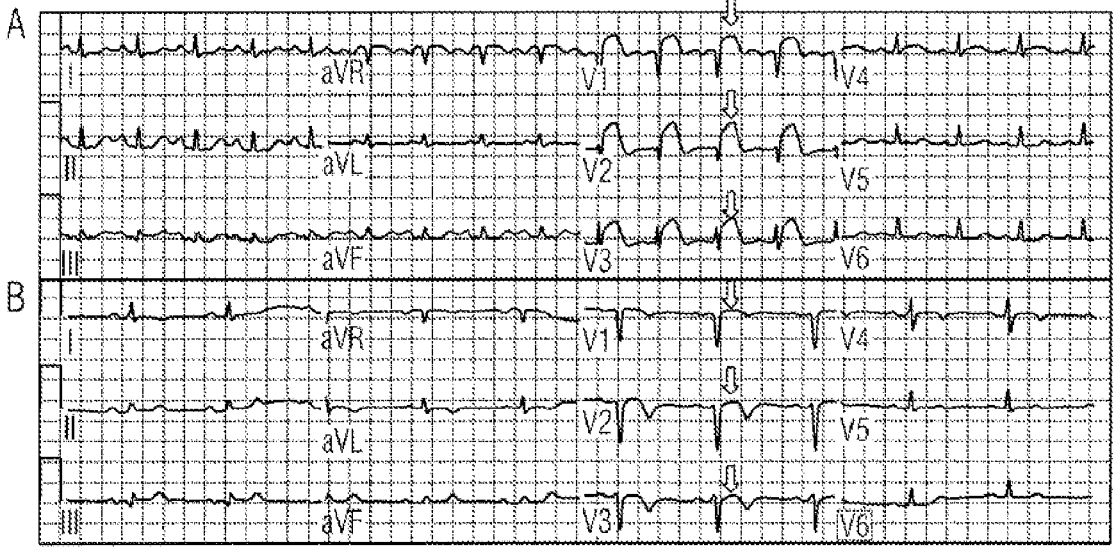
FIG. 6: Electrocardiogram of a patient with STEMI on admission (A) and after successful PPCI (B). Note the ST elevation in A (blue arrows) showing the existence of myocardial ischemia and the resolution of ST elevation (red arrows) in B indicating the restoration of blood flow. In patients with large extent of MVO, ST elevation in ECG after PPCI is not restored indicating persistent myocardial ischemia

These unexpected findings concerning MVO were also supported by other measurements. Changes in ST elevation in electrocardiograms before and after PPCI measured as ST restoration (%) are closely correlated with the extent of MVO (FIG. 6). In fact, recent evidence suggests that incomplete resolution of ST-segment elevation after PPCI in patients with STEMI reflects the presence of microvascular and left ventricular dysfunction, especially in patients with left anterior descending artery (LAD) infarction.

Figure 7:
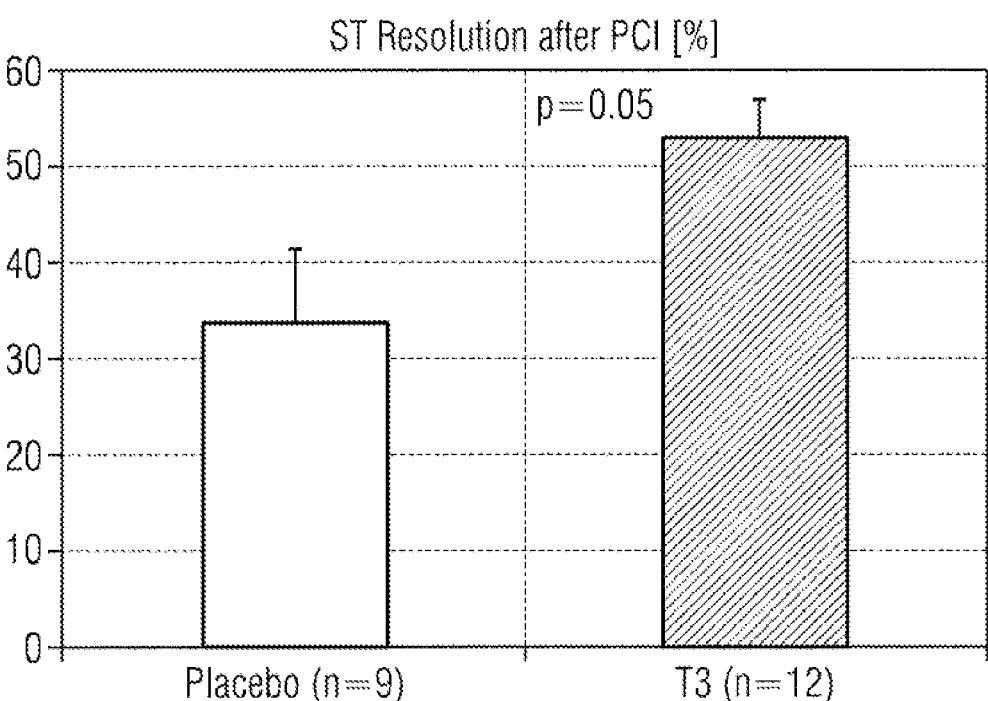
FIG. 7: Resolution of ST elevation (%) in electrocardiograms performed on admission and after PPCI in placebo and T3 groups

The Mean ST resolution after PPCI was found higher in T3 than in the placebo group (FIG. 7). The mean ST resolution was measured 34% in the placebo group compared to 54% in the T3 treated group (p=0.05). These measurements provide strong evidence of the effect of T3 on MVO.

Figure 8:
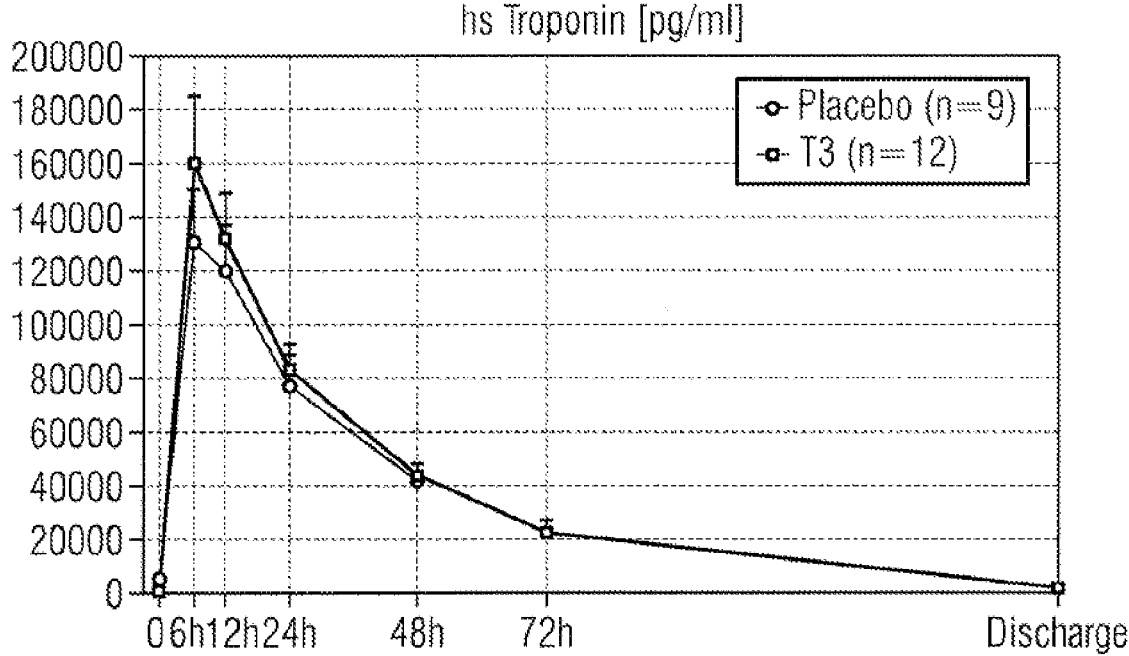
FIG. 8: Troponin levels over time in STEMI patients treated with placebo and T3

Troponin levels in blood over time are mainly a measure of myocardial injury. According to the present invention, troponin levels are similar between T3 and placebo groups indicating a similar infarct size in accordance with CMR data. Thus, it seems that the effect of T3 on MVO is independent from infarct size. (FIG. 8).

Figure 9:
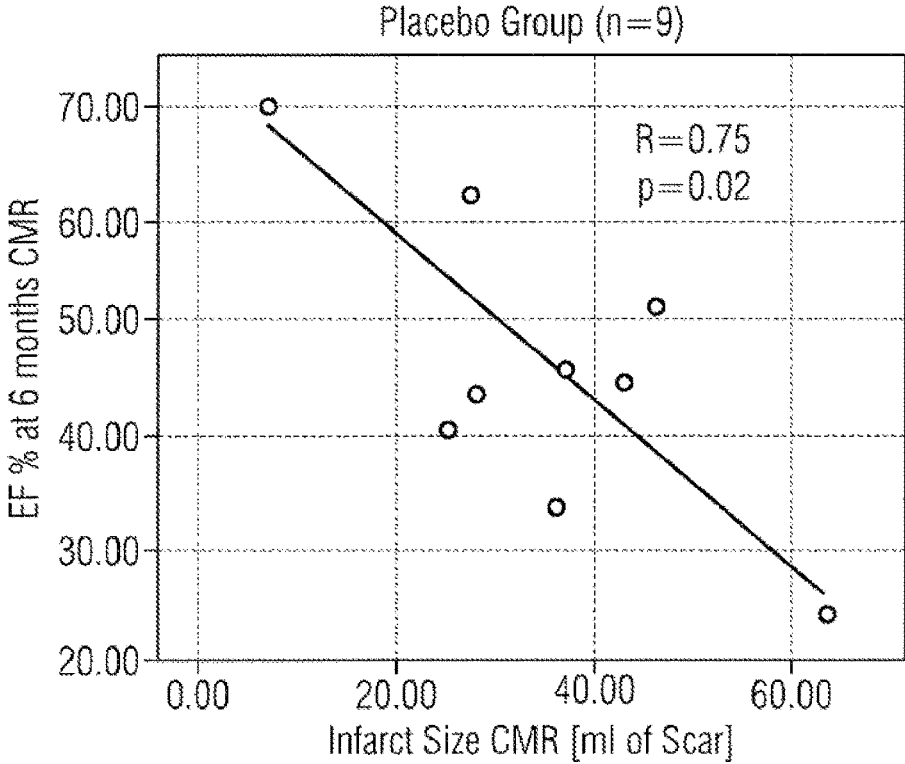
FIG. 9: Correlation of cardiac function (ejection fraction at 6 months) and infarct size measured by CMR in placebo group. There is a strong inverse relationship in accordance with previous studies

Accordingly, T3 treatment was associated with improved cardiac function at discharge and at 6 months. This effect, as our data show, is rather attributed to the effect of T3 on MVO than to infarct size. According to FIG. 9, the functional recovery at 6 months in the placebo group is largely dependent on infarct size. Thus, a higher infarct size results in lower functional recovery at 6 months. This is consistent with prior art.

Figure 10:
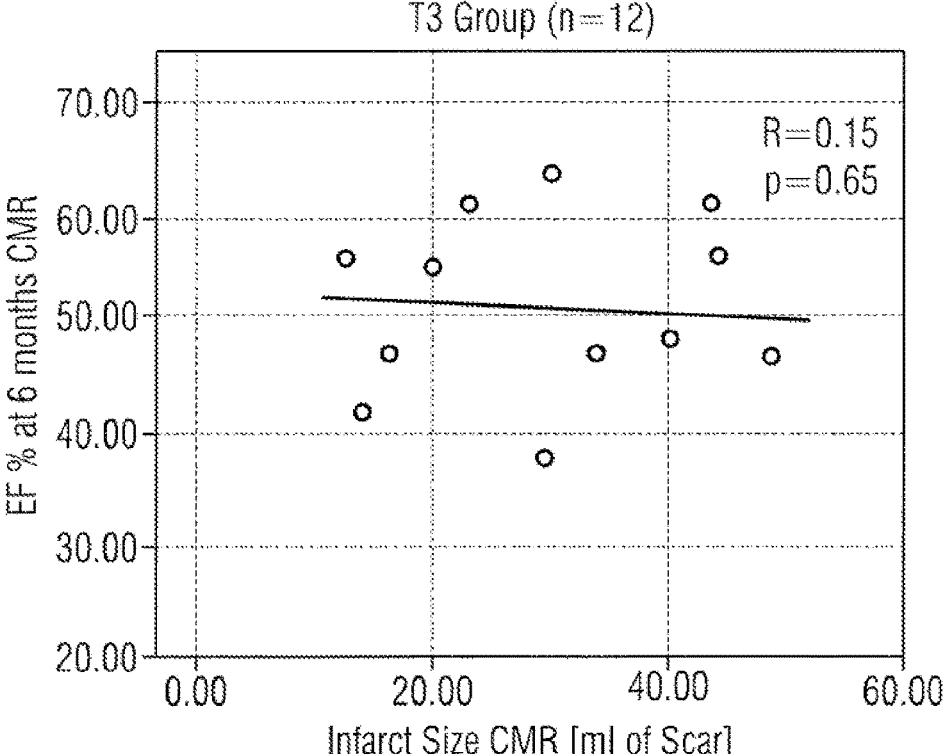
FIG. 10: Correlation of cardiac function (ejection fraction at 6 months) and infarct size measured by CMR in T3 treated

Surprisingly, it was found that in T3 group (FIG. 10), the recovery of function was independent of the myocardial injury indicating other novel effects of T3 on the ischemic myocardium (i.e. effects on MVO). No experimental or clinical study so far has described this particular T3 effect on myocardial healing (repair) after ischemia/reperfusion injury.

Figure 12:
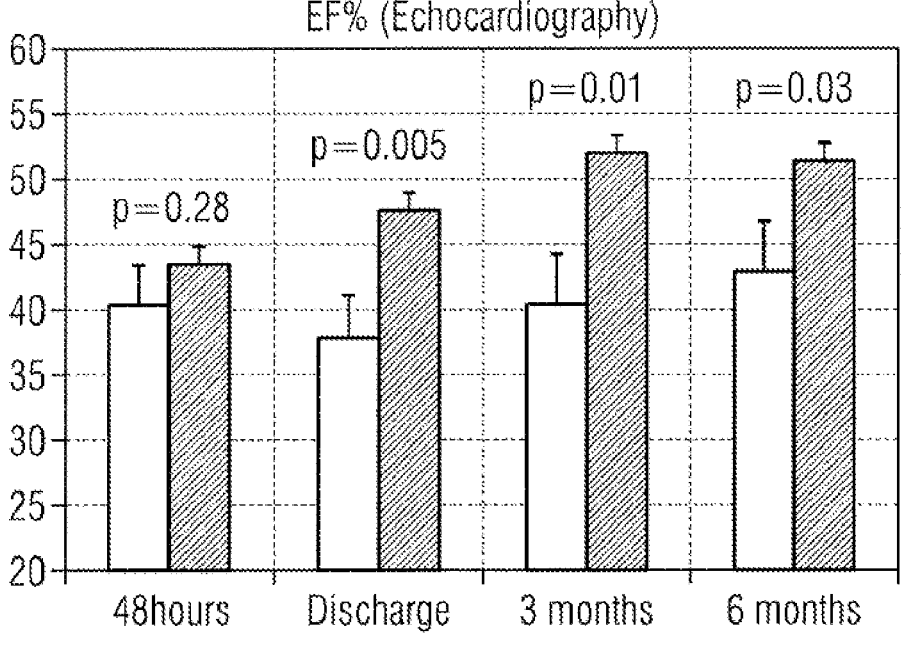

Interestingly it was found that, although CMR clearly indicate that infarct size was similar between the placebo and T3 group (see FIG. 11), echocardiographic data show an improvement of LV ejection fraction in T3 treated STEMI patients early and late after the index event (see FIG. 12).

Additional evidence for the improved myocardial function due to T3 treatment was demonstrated by left ventricular ejection fraction (EF %) and left ventricular end-diastolic (LVEDVi) and end-systolic (LVEDVi) volumes, as these assessed by CMR for T3 group and placebo group at discharge (FIG. 13).

Similarly, improvement of cardiac function in T3 treated patients persisted at 6 months (FIG. 14).

The invention claimed is:

1. A method to prevent or minimize microvascular obstruction (MVO) in a patient comprising administering L-triiodothyronine (T3), wherein the MVO treatment is commenced after primary percutaneous coronary intervention (PPCI), and the PPCI is performed in ST-segment-elevation myocardial infarction (STEMI) patients wherein T3 is administered intravenously as a solution with a concentration of T3 in the range of 5 to 20 µg/ml, after an initial bolus of 0.7 to 0.9 µg T3 per kg weight of the patient, and wherein a level of T3 in patient serum is at least 5.5 ng/ml at 24 hours and at least 4.5 ng/ml at 48 hours after the start of L-triiodothyronine treatment.

2. The method of claim 1 wherein the presence of MVO is measured by cardiac magnetic resonance.

3. The method of claim 1 wherein the patient subsequent to the bolus receives a continuous injection of 0.1 to 0.2 µg/kg/h.

4. The method of claim 1 wherein patients receive in total 350 to 600 µg T3 over about 48 hours.

5. A method for the treatment of microvascular obstruction, comprising:

treating an ST-segment-elevation myocardial infarction patient after primary percutaneous coronary intervention diagnosed with microvascular obstruction, by administering L-triiodothyronine, wherein the patient receives an initial bolus of L-triiodothyronine of 0.7 to 0.9 µg per kg weight of the patient, and subsequent to the bolus receives a continuous injection of 0.1 to 0.2 µg/kg/h of L-triiodothyronine.

6. The method of claim 5 wherein a level of L-triiodothyronine in patient serum is at least 5.5 ng/ml at 24 hours and at least 4.5 ng/ml at 48 hours after the start of L-triiodothyronine treatment.

* * * * *